United States Patent [19]

Bauer

[11] Patent Number: 4,707,171

[45] Date of Patent: * Nov. 17, 1987

[54] PROCESS FOR OBTAINING $C_{2+}$ OR $C_{3+}$ HYDROCARBONS

[75] Inventor: Heinz Bauer, Neuried, Fed. Rep. of Germany

[73] Assignee: Linde Aktiengesellschaft, Wiesbaden, Fed. Rep. of Germany

[*] Notice: The portion of the term of this patent subsequent to Nov. 10, 2004 has been disclaimed.

[21] Appl. No.: 809,958

[22] Filed: Dec. 17, 1985

[30] Foreign Application Priority Data

Dec. 17, 1984 [DE] Fed. Rep. of Germany ....... 3445962
Mar. 29, 1985 [DE] Fed. Rep. of Germany ....... 3511636

[51] Int. Cl.$^4$ .............................................. F25J 3/02
[52] U.S. Cl. .................................... 62/30; 62/20; 62/24; 62/27; 62/28; 62/31; 62/38; 62/39; 208/341; 208/342; 208/343
[58] Field of Search ................... 62/17, 38, 20, 39, 28, 62/30, 31, 34, 27, 24; 208/341, 342, 343

[56] References Cited

U.S. PATENT DOCUMENTS

| 3,932,156 | 1/1976 | Stern | 62/20 |
| 4,272,269 | 6/1981 | Hammond et al. | 62/28 |
| 4,486,209 | 12/1984 | Fabbri et al. | 62/30 |
| 4,507,133 | 3/1985 | Khan et al. | |
| 4,548,629 | 10/1985 | Chi | 62/24 |
| 4,582,517 | 4/1986 | Burr et al. | 62/28 |
| 4,584,006 | 4/1986 | Apffel | 62/30 |
| 4,592,766 | 6/1986 | Kumman et al. | 62/31 |
| 4,596,588 | 6/1986 | Coon | 62/28 |
| 4,597,788 | 7/1986 | Apffel | 62/28 |
| 4,600,421 | 7/1986 | Kumman | 62/34 |
| 4,608,068 | 8/1986 | Bauer et al. | 62/31 |
| 4,617,039 | 10/1986 | Buck | 62/30 |

Primary Examiner—Asok Pal
Attorney, Agent, or Firm—Millen & White

[57] ABSTRACT

For obtaining $C_{2+}$ or $C_{3+}$ hydrocarbons from gas mixtures containing essentially light hydrocarbons and optionally, hydrogen or nitrogen, the gs mixture is first cooled and subjected to a phase separation, and the thus condensed components are fractionated by rectification. The uncondensed portion of the gas mixture along with the overhead product of the rectification after it has been partially condensed, is subjected to treatment in a recontacting column wherein mass transfer and heat transfer occur, and wherein $C_{2+}$ or $C_{3+}$ hydrocarbons are transferred from the gas phase to the liquid phase. The liquid phase thus collected is fed into the rectification column as external reflux while the remaining gas is removed, after heating, as a residual gas.

23 Claims, 4 Drawing Figures

PROCESS FOR OBTAINING $C_{2+}$ OR $C_{3+}$ HYDROCARBONS

CROSS REFERENCE TO RELATED APPLICATIONS

This application is related to concurrently filed, and commonly assigned, applications entitled "Separation of $C_{3+}$ Hydrocarbons by Absorption and Rectification", Sapper, Ser. No. 809,953; "Process for Separation of $C_{2+}$, $C_{3+}$ or $C_{4+}$ Hydrocarbons", Bauer, Ser. No. 809,956; and "Process for the Separation of $C_{2+}$ or $C_{3+}$ Hydrocarbons from a Pressurized Hydrocarbon Stream", Bauer, Ser. No. 809,957, all incorporated by reference herein.

BACKGROUND OF THE INVENTION

This invention relates to a process and apparatus for the separation of $C_{2+}$ or $C_{3+}$ hydrocarbons from a gas stream containing light hydrocarbons, wherein the gas stream, under super atmospheric pressure, is cooled, partially condensed and separated into a liquid and a gaseous fraction, and wherein the liquid fraction is subjected to rectification to obtain a product stream containing essentially $C_{2+}$ or $C_{3+}$ hydrocarbons and a residual gas stream containing predominantly lower boiling components. By light hydrocarbons is generally meant aliphatic hydrocarbons containing 1–5 carbon atoms.

Such processes are used mainly to separate ethane or propane from natural gases or other gases, for example refinery tail gases. In addition, these processes are suitable for the separation of analogous unsaturated hydrocarbons, for example ethylene or propylene, from a gas stream containing these components, for example, refinery tail gases. Reprocessing of refinery tail gases has recently become economically attractive since the market prices for LPG ($C_3/C_4$ hydrocarbon mixtures) have increased while, in contrast, the demand for vacuum residues such as heavy oil has decreased. For this reason, heavy fractions are often burned to cover the internal fuel needs of a refinery whereas the $C_{2+}$ or $C_{3+}$ hydrocarbons which collect in large amounts, especially in the processing of light crude oil components into gasoline, are separated from tail gases.

In an earlier German patent application P 34 08 760.5 filed Mar. 9, 1985, having a common assignee and corresponding substantially to U.S. application Ser. No. 709,742 filed Mar. 8, 1985 by Bauer et al, incorporated by reference herein, a process of this type is disclosed which relates to the separation of $C_{3+}$ hydrocarbons. An important feature of this earlier application resides in the fact that the $C_{3+}$ hydrocarbons to be separated condense out during the partial condensation to such an extent that only the condensate needs to be fed into the rectification, while the uncondensed portions contain so little $C_{3+}$ hydrocarbons that further condensation can be dispensed with. Because of this, the uncondensed portions can be immediately heated again, preferably in indirect exchange with feed gas, and thereafter removed as a residual gas without first having to go through rectification. That leads to more advantageous rectification conditions, particularly since a higher overhead temperature can be used.

SUMMARY OF THE INVENTION

An object of one aspect of this invention is to provide an improved process of the above-mentioned type, especially wherein the yield of $C_{2+}$ or $C_{3+}$ hydrocarbons is increased.

Another object is to provide an installation or apparatus for conducting the improved process.

Upon further study of the specification and appended claims, further objects and advantages of this invention will become apparent to those skilled in the art.

According to the process aspect of this invention, the gaseous fraction separated after partial condensation is fed into a recontacting column in which $C_{2+}$ or $C_{3+}$ hydrocarbons are scrubbed from the gaseous fraction with condensed residual gas obtained from the rectification and the liquid fraction which collects in the bottom of the recontacting column is fed into the rectification. The recontacting column of this invention, hereinafter referred to as the R-C column, is characterized by a number 1 to 10, preferably 2 to 5 theoretical plates.

By this invention, an extensive separation of $C_{2+}$ or $C_{3+}$ hydrocarbons is achieved in the R-C column. This is especially surprising because the condensation of these heavy components still contained in the gaseous fraction is achieved by bringing them into contact with a lighter fraction. Usually, in contrast, to scrub specific hydrocarbons from a gas, hydrocarbons which are heavier than the components to be scrubbed are used as scrubbing agents.

Without being bound by an explanation of the mechanism of this invention, the high yield attainable by the process according to the invention is believed to be attributed to the favorable interaction of several effects. Accordingly, the partially condensed residual rectification gas acts as a cooling agent since, on entering the R-C column, it is expanded from a relatively high partial pressure, under which the condensate was formed, to a low partial pressure so that a part of the condensate reevaporates with the simultaneous release of cold. This cooling leads to a temperature which clearly is below, e.g., by at least 3° K., preferably at least 10° K., the lowest prevailing temperature realized in the partial condensation of the feed gas stream, as a result of which there are condensed further heavy components still remaining in the gaseous fraction from the feed gas partial condensation step. Since, on the other hand, the achievable degree of separation in the R-C column is clearly higher than what might be expected based solely on additional cooling, still other effects, especially solubility effects, must also contribute favorably.

In an advantageous improvement of the invention, the liquid fraction which collects at the bottom of the R-C column is fed into the rectification column as reflux liquid. This eliminates the necessity of producing reflux liquid for the rectification separately, for instance by using an external source of refrigeration.

In a further advantageous improvement of the invention, the overhead product of the R-C column, which generally is delivered as a residual gas after reheating to ambient temperature, is first expanded and then used to cool the head of the R-C column. The additional head cooling of the R-C column leads to a further, increased cooling and thus to a further increase in the yield of the process. The expansion can occur by simply constricting the gas stream in a valve, but with sufficiently large gas streams or with a large portion of light components, for instance with a hydrogen portion higher than 20%, the use of an expansion turbine is also contemplated.

In a further especially advantageous modification of the invention, the gaseous fraction separated after the partial condensation is first cooled to a lower temperature through further indirect heat exchange, before it is fed into the R-C column. The components which thus condense, which contain a relatively high proportion of the $C_{2+}$ or $C_{3+}$ hydrocarbons remaining in the gaseous fraction, are separated and also fed into the rectification, while only the uncondensed portion of the gaseous fraction is fed into the R-C column. This procedure offers advantages especially when the bottom fraction obtained in the R-C column is used as a reflux liquid in the rectification column. The condensed heavier components, e.g., mostly $C_{2+}$ or $C_{3+}$ the gaseous fraction are then separated to a large extent, e.g., at least 30% before the formation of the reflux liquid and can be fed into the rectification at a lower point than the reflux liquid column, thus improving rectification efficiency. In transferring the gaseous fraction from the phase separator to the recontacting column the gaseous fraction is not subjected to any external pressure-reduction stages. Other than normal pressure losses from friction in pipe flow and partial condensation from heat exchange, the pressure of the gaseous fraction is not reduced between the phase separator and the recontacting column.

In an advantageous further development of this modification of the process, the components which condense from the gaseous fraction by indirect heat exchange are fed to the rectification column in the same feed pipe with the liquid fraction obtained by the partial condensation. Of course, separate piping and feeding of both condensate fractions are possible, but the advantages attainable in this way are often so limited as to be not worth the higher equipment expenses. The processing of combined condensate fractions can, on the other hand, be particularly simply designed since the further cooling and partial condensation of the gaseous fraction is conducted simply inside a phase separator which is provided in any case for separating the liquid from the gaseous fraction after the first partial condensation. By placing a heat exchanger in the upper region of the phase separator, a mixing of both condensate fractions is accomplished without any other design measures.

The cooling of the residual gas from the rectification column is conducted at a sufficiently low temperature so that 50 to 99%, especially 70 to 95%, for instance 90% of the residual gas is condensed. With a $C_{3+}$ bottoms separation, the residual gas typically contains small amounts of hydrogen (to the extent that the gas stream contains hydrogen), methane, $C_2$ hydrocarbons as main components and small portions of $C_3$ hydrocarbons, but each individual case depends on the particular composition of the gas stream to be fractionated and the actually employed process conditions. In the case of a $C_2$ separation in the rectification bottoms, the component spectrum shifts to methane as the main component in the residual gas $C_2$ being present only in small amounts and $C_3$ practically not at all. To effect partial condensation, the residual gas is cooled to at least the temperature to which the gas stream, in the framework of its partial condensation, is cooled. For this purpose, the residual gas stream can be advantageously fed through a separate cross section of the heat exchanger used for cooling the crude gas, although cooling in a separate heat exchanger is also possible.

At the head of the R-C column, a markedly lower temperature appears than that of the gas after partial condensation, for instance a temperature 10° to 20° C. lower. To the extent that the gaseous fraction which comes from the head of the R-C column and which is heated as a residual gas and removed from the installation, is fed directly through the heat exchanger used for cooling the crude gas, relatively high temperature differences result at the cold end of this heat exchanger, resulting in relatively high heat losses. To avoid this inefficiency, it is contemplated in another design modification of the invention that at least part of the overhead product of the R-C column first enter into a heat exchange with previously partially cooled or condensed residual gas from the rectification. In this way, not only can large temperature differences at the cold end of the heat exchanger used for cooling the crude gas be avoided, but in doing so a further cooling or condensation of the residual gas of the rectification results as an additional effect.

In a further advantageous modification of the invention, the liquid fraction separated from the crude gas after partial condensation is at least partially heated, before rectification, against the gas stream to be cooled, and the resultant liquid-gas mixture is fed to an appropriate feed point in the rectification column.

In processing gas streams rich in components boiling lower than methane, there is another modification of the invention wherein these components are enriched while $C_1$ and $C_2$ hydrocarbons are separated by partial condensation from the overhead product of the R-C column. This procedure can, for instance, be applied in separating $C_{2+}$ or $C_{3+}$ hydrocarbons and nitrogen from nitrogen-rich natural gas or especially for obtaining said heavy hydrocarbons and hydrogen from hydrogen-rich refinery gases. This type of separation is advantageous, especially when the feedstock stream contains a relatively high amount of low-boiling components, for instance a hydrogen content on the order of magnitude of 50 to 90 mol-%. Such a hydrogen amount is in fact sufficient to produce, by expansion, the cold required for the additional separation without it being necessary to use an additional external source of energy.

In many applications, a further fractionation of the $C_{2+}$ or $C_{3+}$ hydrocarbon product, especially separation of a $C_3/C_4$ hydrocarbon mixture and $C_{5+}$ hydrocarbons, is desirable. For this purpose, according to a preferred design of the process according to the invention, before the formation of the liquid and gaseous fractions the majority of the $C_{5+}$ hydrocarbons is separated from the gas stream, if the concentration of these components is high enough, e.g., at least 1 to 10 mol-% to make such a separation worthwhile.

The $C_{5+}$ separation is conducted in practice by partial condensation at a temperature higher than that at which the above-mentioned liquid and gaseous fractions are formed. By means of preliminary separation of the heavy components, the mixture fed into the rectification column is nearly free of $C_{5+}$ hydrocarbons, so that there is obtained from a subsequent $C_{3+}$ rectification of the liquid fraction, a product stream which is a conventional commercial LPG fraction.

To increase the yield of $C_3$ and $C_4$ hydrocarbons, the separated heavy hydrocarbons are also fed into the rectification column, wherein the introduction of the $C_{5+}$ fraction into the column occurs, according to the equilibrium conditions in the column, below the feed point of the liquid fraction formed by partial condensation and wherein it is furthermore provided that a stream containing essentially $C_3$ and $C_4$ hydrocarbons is removed between the two feeds. By the additional rectification of the $C_{5+}$ fraction, $C_3/C_4$ hydrocarbons condensed or absorbed during the condensation of the $C_{5+}$ fraction are recovered as a product. Between the two feed points, a region of maximal $C_3/C_4$ concentration is formed within the rectification column where the $C_3/C_4$ product stream is advantageously removed.

An installation or apparatus for conducting the process according to the invention includes, as essential parts, at least one heat exchanger for cooling and partially condensing the gas stream, a phase separator for separating the partially condensed portion of the gas stream, a rectification column for fractionating the partially condensed portion of the gas stream, and an R-C column the lower region of which is connected to the vapor chamber of the separator and whose upper region is connected to the head of the rectification column, with a heat exchanger is located between the head of the rectification column and the upper region of the R-C column.

In an especially advantageous structural embodiment, the phase separator and the R-C column have a common housing. Preferably the R-C column is placed above the separator and separated from it by means of a column plate, so that the gaseous fraction leaving the separator can enter the lower region of the R-C column via a riser in a bubble-cap or the like. In another structural embodiment, heat exchange pipes are placed in the upper region of the separator through which cold process streams or other cold fluids can be conducted to condense out the heavy constituents from the gaseous fraction before it is fed into the R-C column.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE DRAWINGS

Figure 1:
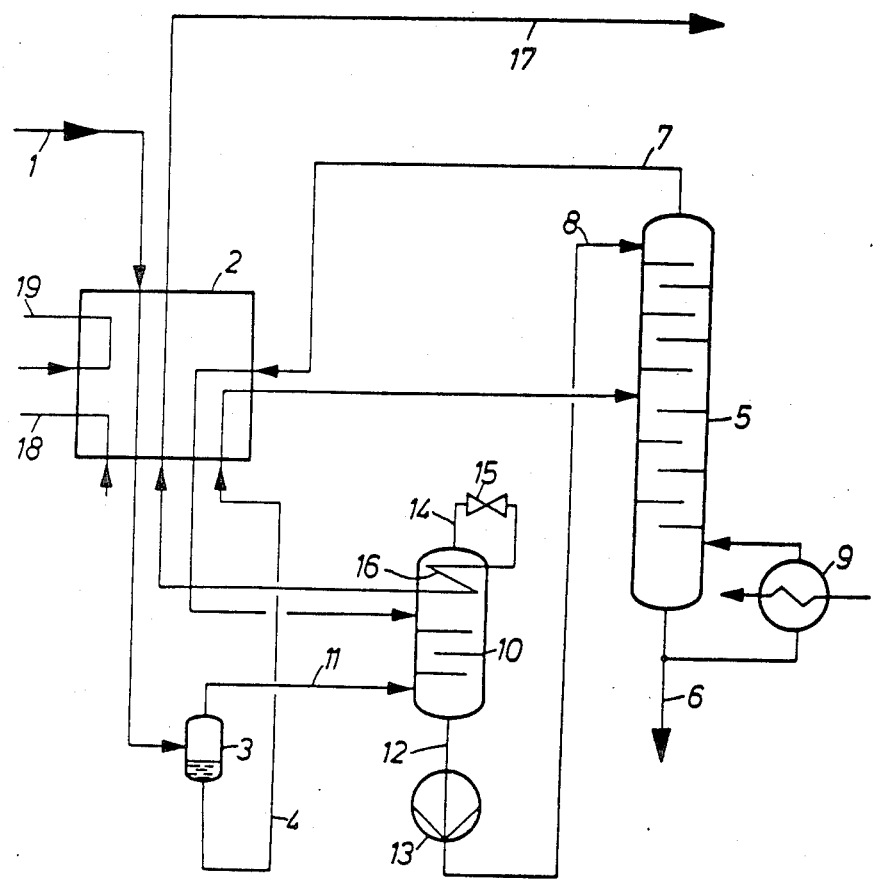
FIG. 1 is a schematic representation of a relatively simple preferred embodiment of the process according to the invention.

In the embodiment shown in FIG. 1, the gas stream feed to be fractionated is fed by pipe 1 to heat exchanger 2 under elevated pressure and at approximately ambient temperature where it is cooled to the extent that most of the hydrocarbons to be separated, that is to say the $C_{2+}$ or $C_{3+}$ hydrocarbons, condense. The partially condensed gas stream is then subjected to a phase separation in a phase separator 3, and the resultant condensate is first passed in conduit 4 to heat exchanger 2 where it is partially vaporized, and the resultant fluid mixture is then fed into a rectification column 5. In rectification column 5, the condensate is fractionated into: (i) a $C_{2+}$ or $C_{3+}$ fraction removed as a product stream by conduit 6 from the bottom of the column, and (ii) a residual gas stream 7 containing lower boiling components. The rectification is conducted using an external reflux introduced by pipe 8 and reboiler which, for instance, is run on low-pressure steam or hot water.

The overhead product from the rectification column, removed by pipe 7, which consists essentially of components boiling lower than the product fraction removed by pipe 6, is fed into heat exchanger 2 and again cooled, whereby higher boiling components still remaining in this gas partially condense. The condensate thus formed occurs in an amount which is greater than the amount of reflux needed for rectification. This partially condensed residual gas is fed into the upper region of a recontacting column 10 in which it is brought into countercurrent contact with the gaseous fraction which was obtained from phase separator 3 via pipe 11. The liquid collecting at the bottom of column 10 is removed by pipe 12 and fed, by pump 13 through pipe 8, into rectification column 5 as external reflux. At the head of the R-C column, a gaseous fraction almost completely devoid of the $C_{2+}$ or $C_{3+}$ hydrocarbons to be separated, is removed by pipe 14. This gas stream is expanded in valve 15 to a desired residual gas pressure, and the cold thus obtained is transferred in a cold trap 16 to the gaseous fraction in R-C column 10. Subsequently, the residual gas is heated to ambient temperature in heat exchanger 2 and finally removed by pipe 17.

The cold trap 16 is an indirect heat exchange means for transferring the cold values obtained from the expansion step.

In a specific example, according to FIG. 1, a crude gas is introduced by pipe 1 at a temperature of 313° K. at 20 bar pressure. It contains 15% hydrogen (percentages below always in mol-%), 3% nitrogen, 37% methane, 26% ethane, 14% propane, 14% butane and 1% pentane. After being cooled in heat exchanger 2 to 237° K. a condensate is separated in phase separator 3 which contains 0.4% hydrogen, 0.2% nitrogen, 9.4% methane, 38.5% ethane, 36.3% propane, 12.1% butane and 3.1% pentane. The remaining gaseous portion, about 68% of the crude gas, is brought into contact, in R-C column 10, with the residual gas from the rectification, also cooled to 237° K. This residual gas from pipe 7 contains 0.5% hydrogen, 0.3% nitrogen, 15.0% methane, 80.8% ethane and 3.4% propane. The overhead product of the R-C column is removed by pipe 14 at a temperature of 221° K., expanded in valve 15 to the pressure of the residual gas and simultaneously cooled to 210° K., heated is cold trap 16 to 218° K. and subsequently heated again in heat exchanger 2 to 310° K. before it is delivered by pipe 17 as residual gas at a pressure of 5 bar. This residual gas contains 18.6% hydrogen, 3.7% nitrogen, 45.8% methane, 31.7% ethane and only 0.2% propane.

The liquid product removed by pipe 12 from the bottom of R-C column 10 consists of 0.3% hydrogen, 0.2% nitrogen, 10.5% methane, 74.0% ethane, 14.2% propane, and 0.8% butane and pentane. It is fed into the head of rectification column 5 operated at 18 bar. In the bottom of the rectification column, a $C_{3+}$ product stream is withdrawn via pipe 6, said product stream containing 2.0% ethane, 71.9% propane, 20.9% butane and 5.2% pentane. The yield of $C_{3+}$ in this process is about 98.9%.

Figure 2:
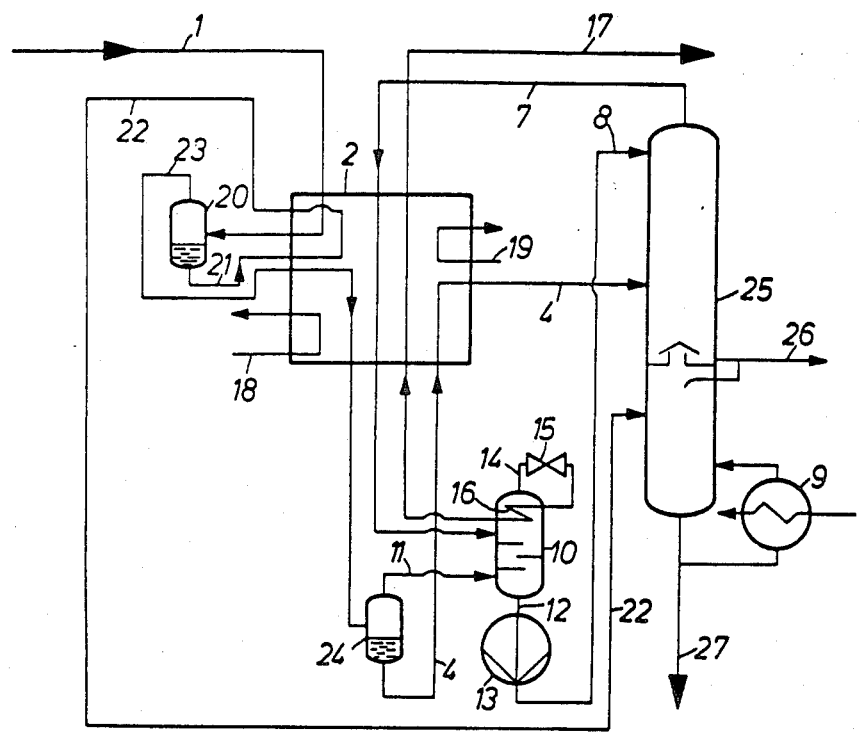
FIG. 2 is a schematic representation of a preferred embodiment of the process according to the invention wherein a $C_{5+}$ separation is incorporated in the flowsheet.

The embodiment represented in FIG. 2 is a variant of the process according to the invention wherein a $C_{5+}$ separation from the gas mixture is carried out in a first step of the process. For this purpose, feed stream 1 is first cooled in heat exchanger 2 only sufficiently to condense out most (e.g., at least 70%) of the $C_{5+}$ components. The partially cooled mixture from heat exchanger 2 at an intermediate temperature is passed to phase separator 20, wherein the condensed fraction is withdrawn via pipe 21, and after partial heating in heat exchanger 2 is passed by conduit 22 to a rectification column 25. The remaining gaseous fraction from phase separator 20 is cooled via pipe 23 in heat exchanger 2 and ultimately fed into phase separator 24, which corresponds to phase separator 3 of the previously described embodiment of FIG. 1.

The rectification of the condensates separated in phase separators 20 and 24 occurs in a rectification column 25 which, in contrast to the rectification column used in the previous example, exhibits a larger number of plates, e.g., about 20 to 50 plates as compared to 10 to 30, or about 50 to 100% more plates. Between the two feed pipes 4 and 22, a discharge pipe 26 is located in the column at the point where the highest $C_3/C_4$ concentration is found. In the bottom of column 25 a liquid collects which contains essentially $C_{5+}$ hydrocarbons and which is removed as a product stream by pipe 27. A light fraction containing essentially $C_1$ and $C_2$ hydrocarbons is removed from the head of column 25 by pipe 7 as in the previous example.

In this process the heavy portions which have been separated in phase separator 20 are also fed into the rectification. In this way, with relatively low cost, a very high yield of $C_3$ and $C_4$ hydrocarbons can be achieved.

Figure 3:
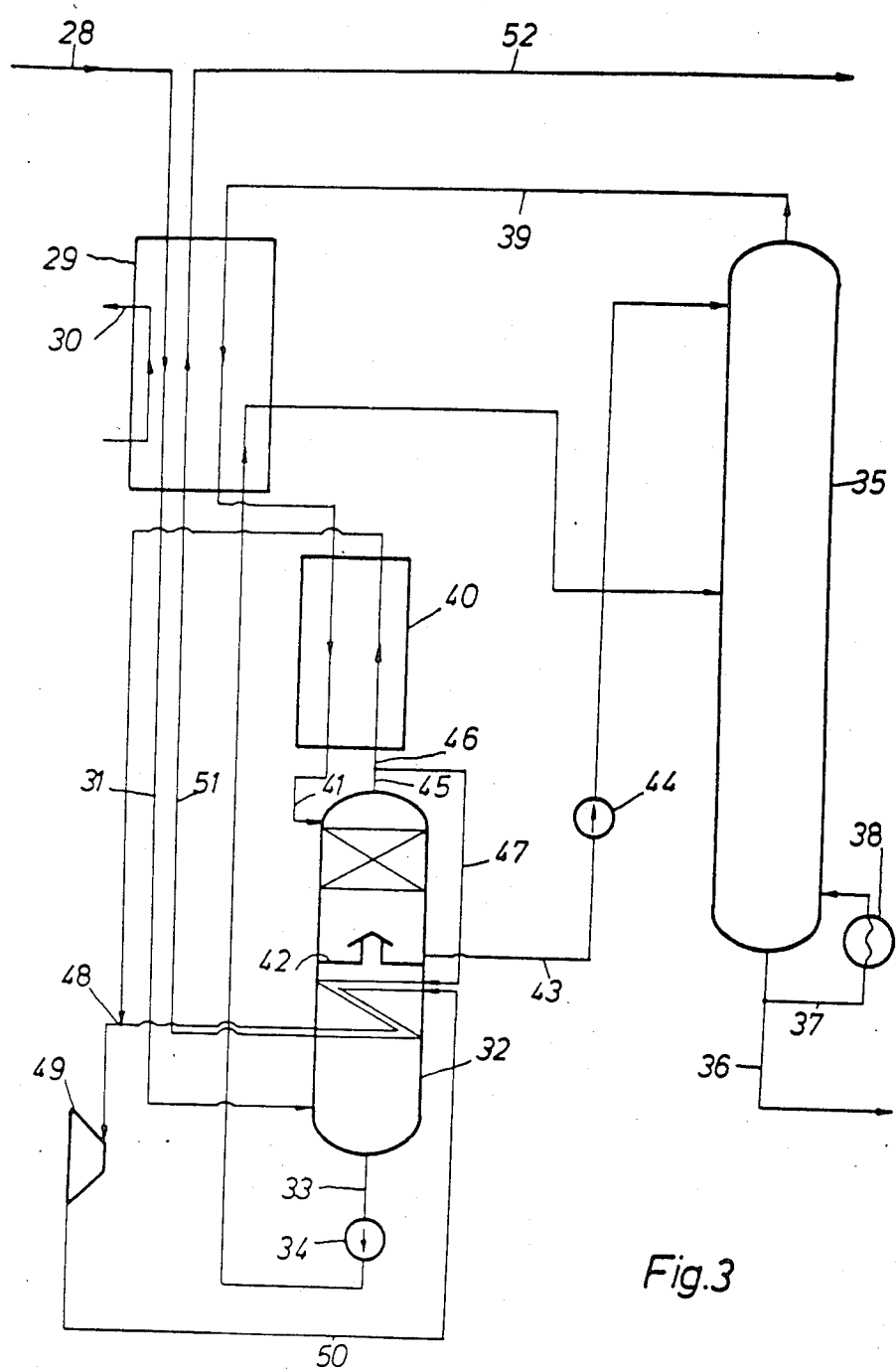
FIG. 3 is a schematic embodiment of the process according to the invention in which the phase separator and the R-C column are combined into one structural unit and overhead gas from the R-C column is subjected to engine expansion.

In the embodiment shown in FIG. 3, a crude gas is introduced by pipe 28 at a temperature of 305° K. and a pressure of 28.9 bar. It contains 67.5% hydrogen, 11.8% methane, 8.8% $C_2$, 7.8%, $C_3$, 3.3% $C_4$ and 0.8% $C_{5+}$ hydrocarbons. After being cooled in heat exchanger 29 to a temperature of 230° K., by indirect heat exchange with process streams to be heated and by an external cooling cycle indicated diagrammatically by pipe 30, the partially condensed mixture is fed by pipe 31 into a phase separator placed in the lower part of a vessel 32 also housing an R-S column in the upper part thereof. Liquid removed from the phase separator by pipe 33 contains 1.4% hydrogen, 3.5% methane, 23.0% $C_2$, 45.1% $C_3$, 21.5% $C_4$ and 5.5% $C_{5+}$ hydrocarbons. By pump 34, the bottom liquid is fed first to heat exchanger 29 at a pressure of 30 bar and, after partial heating, is fed into the rectification column 35.

In rectification column 35, the phase separated liquid is fractionated into a $C_{3+}$ bottom fraction and a $C_{2-}$ fraction. The $C_{3+}$ hydrocarbons are removed by pipe 36 as a bottoms product stream. A partial stream thereof is branched off by pipe 37, heated in reboiler 38 and fed back into the lower region of column 35 to heat the bottom. The product in pipe 36 collects at a temperature of 362° K. at a pressure of 29 bar and consists of 2.0% $C_2$, 63.6% $C_3$, 27.5% $C_4$ and 6.9% $C_{5+}$ hydrocarbons. At the head of rectification column 35, a fraction collects which contains 2.8% hydrogen, 8.7% methane, 84.4% $C_2$ and 4.1% $C_3$ hydrocarbons. This fraction is withdrawn via pipe 39 and cooled before being fed into the R-C column. The cooling occurs first in heat exchanger 29 to a temperature of 202° K. The resultant mostly condensed fraction is fed by pipe 41 into the upper part of vessel 32 at the head of the R-C column. A liquid collects in the lower region of the R-C column on column plate 42, which separates the R-C column from the phase separator underneath it. This liquid on plate 40 contains on the one hand, the overhead product from rectification column 35 to the extent that it is condensed in heat exchangers 29, 40 and not reevaporated in the R-C column and, on the other hand, the heavy components scrubbed from the gaseous fraction passed upwardly through plate 42 into the R-C column. The liquid which collects on column plate 42 is removed by pipe 43 and is introduced, by pump 44, into the head of rectification column 35 as a reflux liquid. This reflux liquid collects at a temperature of 200° K. and consists of 1.5% hydrogen, 6.0% methane, 78.6% $C_2$, 13.6% $C_3$ and 0.3% $C_4$ hydrocarbons.

In the R-C column, a residual gas is withdrawn via pipe 45, and then divided into two partial streams. Via pipe 46 a first partial stream reaches heat exchanger 40, where it is used to cool the overhead fraction from the rectification column from about 230° K. to 202° K., whereas the other partial stream is passed through the upper region of the phase separator by pipe 47 to transfer its peak cold by indirect heat exchange with the gaseous fraction in the phase separator. The partial stream in pipes 46 and 47 are then reunited at 48 and engine expanded in a turbine 49 to such an extent that the delivery pressure to be maintained for the residual gas is substantially maintained at the outlet side of the turbine. The residual gas cooled during the engine expansion to 190° K. is first passed via pipe 50 through the vapor chamber of the phase separator, and then is passed by pipe 51 to heat exchanger 29 where it is heated against process streams to be cooled, to a temperature of 302° K. before it is withdrawn via pipe 52 at a pressure of 17 bar. This residual gas contains 76.8% hydrogen, 13.3% methane, 9.8% $C_2$ and 0.1% $C_3$ hydrocarbons.

With this process, 99.5% of the $C_{3+}$ hydrocarbons contained in the crude gas collects in the bottom of the rectification column 35 and is removed via pipe 36 as a product.

Figure 4:
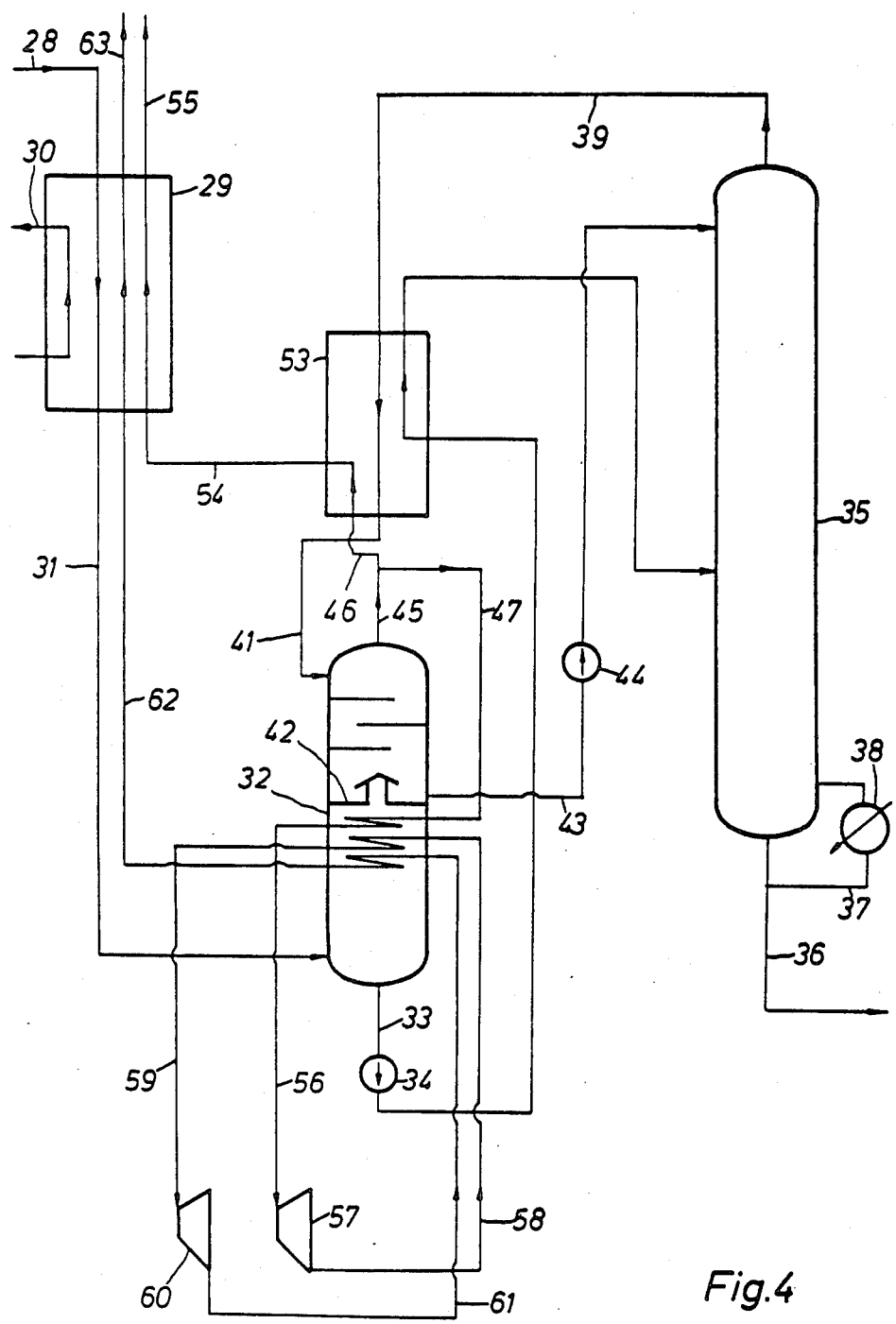
FIG. 4 is a schematic representation of a preferred modification of FIG. 3 wherein two engine expansion steps are utilized.

The process shown in FIG. 4 represents a variation in the process of FIG. 3; therefore, primarily the differences between the two processes will be described. According to FIG. 4, the overhead product from rectification column 35 is fed to a heat exchanger 53 by pipe 39, in which it is cooled first against the bottoms product from the phase separator (said bottoms being heated before being fed into rectification column 35) and then against the overhead product from the R-C column branched off conduit 45 via pipe 46. After being withdrawn from heat exchanger 53, partial stream 46 of the overhead product from the R-C column is fed directly, by pipe 54, to heat exchanger 29 where it is heated to ambient temperature, and removed by pipe 55 substantially at the pressure of the R-C column (diminished in pressure only because of unavoidable pressure losses in the pipes and heat exchangers). Another partial stream of the overhead product from the R-C column is branched from conduit 45 via pipe 47, e.g., at about 200° K., reheated in the upper region of the phase separator to about 220° K. and then fed, by pipe 56 to a first expansion turbine 57 and expanded to an intermediate pressure and a temperature of e.g., about 180° K. The cold thus obtained is also transferred to the gaseous fraction in the phase separator by passing the turbine output via pipe 58, through the upper region of the phase separator via a heat exchanger disposed therein. The resultant heated turbine effluent is fed by pipe 49 to a second expansion turbine and again cooled by substantially isentropic expansion to a temperature of about, e.g., 180° K. The resultant cold residual gas is again fed into the upper region of the phase separator and again transfers its peak cold to the gaseous fraction therein before it is ultimately fed to heat exchanger 29 via pipe 62 and removed as a low-pressure residual gas by pipe 63.

The rectification conditions, especially pressure and temperature, in obtainin $C_{2+}$ or $C_{3+}$ hydrocarbons are usually adjusted on the basis of the usual parameters, especially with regard to the composition of the mixture to be rectified. Furthermore, the gas mixture to be fractionated can also be available under differing conditions, especially at varying degrees of high pressure. In individual cases, therefor, the separation process can be conducted under optimal conditions in such a way that the pressure in the rectification is higher or lower than the pressure of the partially condensed gas stream. In the embodiments according to FIGS. 1 to 4 it is assumed that no significant pressure differences exist. If they should exist in an individual case, the process described can easily be adapted to the altered conditions, for example in the case of rectification under higher pressure, by placing a pump in pipe 4, replacing feed pump 13 by a pump with a correspondingly higher compression ratio and by expanding the partially condensed residual gas into R-C column 10 (FIGS. 1 and 2).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the separation of higher boiling hydrocarbons from a feed gas stream containing light hydrocarbons, said process comprising the steps of:
    (a) the feed gas stream, under superatmospheric pressure, is cooled, partially condensed and separated into a liquid fraction and a gaseous fraction; and
    (b) said liquid fraction is delivered to a rectification column and subjected to rectification to obtain a product stream containing an enriched proportion of higher boiling hydrocarbons and a residual gas stream containing predominantly lower boiling components, wherein the improvement comprises,
    (c) delivering said gaseous fraction to a recontacting column to scrub out higher boiling hydrocarbons from the gaseous fraction, said recontacting column having a bottom portion and a top portion, said gaseous fraction being delivered to said recontacting column without substantial reduction of pressure;
    (d) partially condensing said residual gas to form a resultant partial condensate and delivering said residual gas stream to said recontacting column wherein said resultant partial condensate is employed as a scrubbing agent for the scrubbing step; and
    (e) passing resultant liquid fraction from the bottom portion of the recontacting column to the rectification column.

2. A process according to claim 1, wherein the resultant liquid fraction from the bottom portion of the recontacting column is fed into the rectification column as reflux liquid.

3. A process according to claim 1, further comprising withdrawing an overhead product from the recontacting column, expanding said overhead product, thereby cooling same, and then recycling the cooled overhead to the top portion of the recontacting column.

4. A process according to claim 1, wherein the partial condensation of the feed gas stream in step (a) and partial condensation of the residual gas stream in step (d) are attained by cooling both streams to the same temperature level.

5. A process according to claim 1, wherein the gaseous fraction separated after partial condensation is first cooled and further partially condensed by indirect heat exchange to form a condensate, separating the condensate, passing the separated condensate into the rectification column and passing uncondensed gaseous fraction into the recontacting column.

6. A process according to claim 3, wherein the gaseous fraction separated after partial condensation is first cooled and further partially condensed by indirect heat exchange to form a condensate, separating the condensate, passing the separated condensate into the rectification column and passing uncondensed gaseous fraction into the recontacting column.

7. A process according to claim 5, wherein the condensate obtained from the gaseous fraction through indirect heat exchange is introduced into the rectification column conjointly with the liquid fraction obtained through partial condensation.

8. A process according to claim 5, wherein the indirect heat exchange occurs in the upper region of a phase separator provided for the separation of the liquid and gaseous fractions.

9. A process according to claim 1, wherein the residual gas obtained during rectification is 50 to 99% liquefied before being fed into the recontacting column.

10. A process according to claim 1, wherein the residual gas obtained during rectification is 70 to 95% liquefied before being fed into the recontacting column.

11. A process according to claim 9, wherein the residual gas is mostly liquefied in a final stage of heat exchange by indirect heat exchange with the gaseous fraction withdrawn from the recontacting column.

12. A process according to claim 1, further comprising heating the liquid fraction in indirect heat exchange against the feed gas stream to be cooled.

13. A process according to claim 3, wherein said feed gas stream contains components boiling lower than methane and, before expanding the overhead product from the recontacting column, further comprising separating $C_{1+}$ hydrocarbons from said components boiling lower that methane by partial condensation of said overhead product.

14. A process according to claim 6, wherein said feed gas stream containing components boiling lower than methane and, before expanding the overhead product from the recontacting column, further comprising separating $C_{1+}$ hydrocarbons from said components boiling lower than methane by partial condensation of said overhead product.

15. A process according claim 1, wherein said feed gas contains $C_{5+}$ hydrocarbons, and further comprising separating a major portion of the $C_{5+}$ hydrocarbons before the formation of the liquid and gaseous fractions.

16. A process according to claim 15, further comprising passing the separated $C_{5+}$ hydrocarbons into the rectification column at a feed point below the feed point of the liquid fraction formed by partial condensation, and withdrawing a stream containing essentially $C_3$ and $C_4$ hydrocarbons as a side stream between the two feed points.

17. A process according to claim 1, wherein rectification step (b) is performed at about the inlet pressure of the feed gas stream.

18. A process according to claim 1, wherein said higher boiling hydrocarbons are $C_{2+}$-hydrocarbons.

19. A process according to claim 17, wherein said higher boiling hydrocarbons are $C_{2+}$-hydrocarbons.

20. A process according to claim 1, wherein said higher boiling hydrocarbons are $C_{3+}$-hydrocarbons.

21. A process according to claim 17, wherein said higher boiling hydrocarbons are $C_{3+}$-hydrocarbons.

22. A process according to claim 1, wherein separation step (a) and recontacting step (c) are preformed in a common housing having a lower portion comprising a separator for said separation step (a) and an upper portion comprising a recontacting column for said recontacting step (c), and wherein said gaseous fraction passes from said lower portion through a plate directly into said upper portion.

23. A process according to claim 1, further comprising withdrawing an overhead product from said recontacting column; delivering at least a portion of said overhead product to separation step (a) wherein said overhead product undergoes indirect heat exchange with said gaseous fraction; withdrawing said overhead product from separation step (a) and expanding said overhead product thereby cooling same; and delivering expanded overhead product to separation step (a) wherein said expanded overhead product undergoes indirect heat exchange with said gaseous fraction.

* * * * *